United States Patent [19]

Powell et al.

[11] 4,361,545

[45] Nov. 30, 1982

[54] SOLID PHARMACEUTICAL FORMULATIONS FOR SLOW, ZERO ORDER RELEASE VIA CONTROLLED SURFACE EROSION

[75] Inventors: David R. Powell; Vithal K. Patel, both of Baudette, Minn.

[73] Assignee: Rowell Laboratories, Inc., Baudette, Minn.

[21] Appl. No.: 258,133

[22] Filed: Apr. 27, 1981

Related U.S. Application Data

[63] Continuation-in-part of Ser. No. 40,789, May 21, 1979, Pat. No. 4,264,573.

[51] Int. Cl.$^3$ .............................. A61K 9/22; A61K 9/26
[52] U.S. Cl. .......................................... 424/19; 424/22
[58] Field of Search ..................................... 424/19–22

[56] References Cited

U.S. PATENT DOCUMENTS 4,264,573  4/1981  Powell et al. .......................... 424/19

OTHER PUBLICATIONS

Robinson, M. Chapter 14—Sustained Action Dosage Forms, pp. 439–465 in Lachman et al. (Ed.), The Theory and Practice of Industrial Pharmacy 2nd Ed. (1976) Lea & Febiger, Phila., Pa.

Primary Examiner—Shep K. Rose
Attorney, Agent, or Firm—Millen & White

[57] ABSTRACT

A new class of solid pharmaceutical formulations enables the attainment of slow, zero order in vivo release of a wide range of pharmaceutically active ingredients upon oral administration. A broad range of release rates can be preselected by suitable adjustments of tablet properties. The formulations are based upon control of active ingredient release from the surface of the tablet via a controlled surface erosion mechanism. These compositions comprise:

(a) an effective amount in the range of 10–90 wt % of a pharmacologically active compound having a water solubility (20° C.) of 1/5–1/500 (w/w);
(b) 1–40 wt % of a compound which is pharmaceutically acceptable in oral compositions and has a water solubility (20° C.) of 1/1–1/40 (w/w);
(c) 2–20 wt % of a compound which is pharmaceutically acceptable in oral compositions and has a water solubility (20° C.) of 1/1–1/10 (w/w);
(d) an amount in the range of 0.05–1.0 wt % of a disintegrating agent for pharmaceutical compositions, at which amount the compound is ineffective as a disintegrating agent;
(e) 0.1–2.0 wt % of a surfactant which is pharmaceutically acceptable in oral compositions; and, if necessary for tablet manufacturing purposes,
(f) 1–20 wt % of a binder which is pharmaceutically acceptable in oral compositions; or
(g) 0.5–5.0 wt % of a die wall lubricant which is pharmaceutically acceptable in oral compositions.

17 Claims, 5 Drawing Figures

SOLID PHARMACEUTICAL FORMULATIONS FOR SLOW, ZERO ORDER RELEASE VIA CONTROLLED SURFACE EROSION

CROSS REFERENCE TO RELATED APPLICATIONS

This application is a continuation in part of U.S. application Ser. No. 040,789, filed on May 21, 1979, now U.S. Pat. No. 4,264,573.

BACKGROUND OF THE INVENTION

The present invention relates to solid pharmaceutical formulations whereby, upon oral administration, the active ingredients are released with a slow, zero order selectable rate.

Various techniques are known for formulating active ingredients to selectively control the resultant release rate of the drug, e.g., via sustained release, slow release, fast release, etc.

It is important for any pharmaceutical formulation technique to provide the capability of preselecting a desired release rate which can be tailored to the unique characteristics of each drug. For example, many formulations exist which permit selection of very slow release rates, i.e., sustained release formulations. (See, e.g., U.S. Pat. No. 3,641,236 based upon glycerol fatty acid esters and U.S. Pat. No. 3,950,508 based upon alkyl celluloses and inert powders such as talc, which, in combination with other ingredients, produce a gradual disaggregation of the sustained release tablet.) These can often cause toxicity and other side effects due to an inordinately long presence of the drug in the body. Thus, methods of preselecting somewhat faster release rates, i.e., slow release rates—midway between fast and sustained rates—are needed.

Moreover, as Zaffaroni has suggested (*Therapeutic Implications of Controlled Drug Delivery, Future Trends in Therapeutics*, Ed. F. C. McMahon, Mount Kisco, N.Y., Futura Publishing, 1978, pp. 143-160), an ideal drug delivery system would allow a constant amount of drug to be absorbed per unit of time (zero-order kinetics). Thus, serum concentrations would not fluctuate under steady-state conditions. Weinberger et. al., *The New England Journal of Medicine*, Vol. 299, No. 16, Oct. 19, 1978, pp. 852-857, have stated: "Modern technology related to controlled oral delivery systems should be applied to theophylline in an attempt to approximate zero-order absorption so that the continuous stabilizing effect of this drug on the airways can be maintained in the most effective, convenient and risk-free manner." Similar sentiments have been echoed by many pharmaceutical researchers in recognizing the preference for and importance of zero order release rates. See, e.g., U.S. Pat. No. 3,965,255. Nevertheless, zero order release has rarely been achieved; there is no available technique by which a selected drug can be systematically formulated to provide zero order release kinetics in vitro or in vivo.

Figure 1:
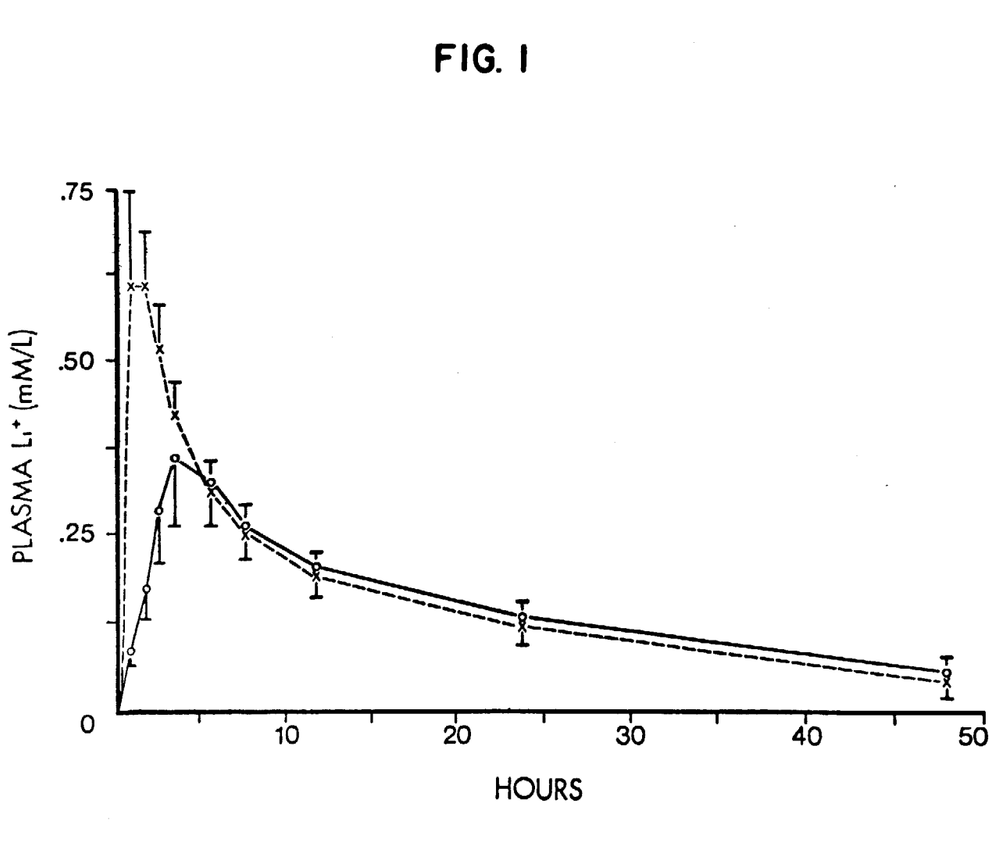
FIG. 1 shows the in vivo plasma concentrations (mean curve ± S.D.) achieved as a function of time upon a single oral dose (12 human subjects-crossover design) of the conventional fast release Lithium formulation X------X, and of the slow release formulation o——o of this invention.

Furthermore, many formulations result in a bioavailability curve having a high concentration peak at the beginning of release with a subsequent tailing off at longer times (see, e.g., curve (-----) of FIG. 1). Such concentration peaks are generally undesirable since they can lead to toxicity and/or other adverse side effects. Additionally, they significantly limit the freedom to increase the unit dosage of administration. Such an increased dosage would correspondingly increase the peak concentration. Under such circumstances, it is not possible to decrease the frequency of administration by increasing the unit dosage. This is a significant disadvantage in view of the well established correlation between the likelihood that a patient will fail to take doses of his medication and the required frequency of administration. Zero order release would attenuate this adverse effect by regulating the amount of active ingredient released in vivo per unit of time.

As can be seen, in most instances, it is desirable to achieve a relatively slow, zero order release rate of medication. This precise rate should be easily selectable so that the resultant in vivo absorption is desirably controlled and the bioavailability of the drug is maximized.

SUMMARY OF THE INVENTION

Accordingly, it is an object of this invention to provide slow release pharmaceutical formulations the amounts of whose ingredients can be readily adjusted to provide in vivo, zero order release for the active ingredient(s).

It is another object of this invention to provide such pharmaceutical formulations by which the release rate and release curve shape can be controlled in order to maximize in vivo bioavailability of the active ingredient and/or minimize side effects.

It is still another object of this invention to provide such formulations which can be reproducibly manufactured by conventional pharmaceutical methodology.

Upon further study of the specification and appended claims, further objects and advantages of this invention will become apparent to those skilled in the art.

These objects have been attained by providing a solid, orally administrable pharmaceutical composition from which the active ingredient has a slow, zero order in vivo release rate when administered orally, comprising:

(a) an effective amount in the range of 10-90 wt % of a pharmacologically active compound having a water solubility (20° C.) of 1/5-1/500 (w/w);

(b) 1-40 wt % of a compound which is pharmaceutically acceptable in oral compositions and has a water solubility (20° C.) of 1/1-1/40 (w/w);

(c) 2-20 wt % of a compound which is pharmaceutically acceptable in oral compositions and has a water solubility (20° C.) of 1/1-1/10 (w/w);

(d) an amount in the range of 0.05-1.0 wt % of a disintegrating agent for pharmaceutical compositions, at which amount the compound is ineffective as a disintegrating agent;

(e) 0.1-2.0 wt % of a surfactant which is pharmaceutically acceptable in oral compositions; and, if necessary for tablet manufacturing purposes, (f) 1-20 wt % of a binder which is pharmaceutically acceptable in oral compositions; or (g) 0.5-5.0 wt % of a die wall lubricant which is pharmaceutically acceptable in oral compositions, the pharmacologically active compound thus having a slow, zero order in vivo release rate when administered orally.

In another aspect, this invention provides a method of orally administering an active ingredient to a patient in need of treatment therewith, such that the drug is released in vivo with a slow, zero order release rate, comprising orally administering a pharmaceutical composition of this invention to such a patient.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DISCUSSION

The mechanism by which the active ingredient is released from the pharmaceutical compositions of this invention can be described as controlled surface erosion. The tablet becomes uniformly smaller and smaller as it erodes and dissolves, but essentially maintains its original overall shape. Tests have shown that tablet cores retain their identity through at least 90% of the dissolution process and that dissolution is a surface controlled phenomenon.

Of course, as a tablet dissolves, the surface area becomes smaller, thereby decreasing the amount of active ingredient available for release from the outer plane per se. In the formulations of this invention, the offsetting physical phenomenon which enables a constant release of active ingredient is an inversely proportional increase in the penetration depth of the surrounding liquid medium. The increased thickness of active ingredient available for release offsets the decreased surface area. This surprising penetration effect is achieved by the overall combination of the required ingredients, but primarily depends upon the presence of two new classes of pharmaceutical excipients, denoted as surface controller (ingredient (b)) and erosion controller (ingredient (c)). It is these two which provide the even, controlled erosion from the tablet surface region whereby the constant controlled rate is achieved.

The selectable dissolution rates generally fall within the realm of slow release rates as conventionally defined. That is, via the pharmaceutical formulations of this invention, the drug becomes bioavailable at a significantly slower rate than typical fast release (disintegrating) dosage forms, but at a rate significantly faster than conventional sustained release products. Thus, the inventive pharmaceutical compositions produce rates which are in the intermediate range. Without intending to limit the scope of this invention in any way, typical slow release dissolution rates may be quantified as those which permit about 0.25–1.0% of the active ingredient to be released and dissolved per minute as measured by the U.S.P. basket method (XIX U.S.P. 651, the basket being rotated at 150 rpm).

Because zero order release rates are obtained, the amount of drug in solution at any time can be predicted from the weight of the undissolved tablet. In tests, it has been shown that at least 98% of the total content of the active ingredient can be accounted for in accordance with this theory. (The amount of drug not accounted for was assumed to reside in undissolved granules or particles which had eroded from the tablet but had not yet dissolved.) Thus, the in vitro dissolution rate in general will obey the following relationship:

$$C_t = C_o - Kt$$

wherein $C_o$ is the initial amount of drug in the tablet; $C_t$ is the amount of drug remaining undissolved, at time (t); K is the zero-order rate constant; and t is the time.

Tests have also shown that $C_t$ may be approximated by simply determining the weight of the core which remains at any given time as follows:

$$C_t \approx C_{ta} = C_o W_t / W_o$$

wherein $C_{ta}$ is the approximated value;

$W_t$ is the core weight remaining at time t; and $W_o$ is the initial weight of the tablet.

Since these formulae fit the observed data well (e.g., see the Examples), the release of the drug with subsequent rapid dissolution is shown to be a surface-controlled phenomenon and release and dissolution obey a zero-order rate equation, i.e., the dissolution rate is independent of the concentration dissolved or remaining.

The exact nature of the surface dissolution, of course, is a function of the overall physical and chemical effects of the combination of all ingredients in the pharmaceutical formulation, including the active ingredient. These effects relate to the ultimate wettability, penetrability, cohesion and erosion of the resultant tablet and, in essence, govern the ultimate dissolving rate. Each ingredient generally has a major effect on one tablet property, but may also play secondary and tertiary roles.

One of the principal characteristics of the ingredients required in the pharmaceutical composition of this invention is that they are essentially of a water soluble nature and do not include gums, pH-dependent excipients, waxes, fats or the polymers usually associated with sustained release products. Generally, the only polymer employed is the binder. Additionally, the release effects are attained without layers, beads or enteric materials within the product. As a result, the tablet can be readily manufactured by conventional techniques using standard equipment.

The above described amounts and solubilities of ingredients are tailored in view of each other so that the desired slow, zero order release will be obtained. It is possible that one or more of the stated solubility and/or percent content ranges may be varied somewhat so that the resultant new combination will still produce the desired release characteristics. All such combinations are, of course, equivalents and included within this invention. Furthermore, more than one formulation within the stated limits can provide a particular zero order rate for a given dosage of a particular drug.

As can be seen from the following description, there is some overlap among the classes of ingredients. This provides an advantageous latitude for selecting compatible excipients for a wide range of drugs for each of the ingredient classes required by this invention. In essence, any ingredient listed in the U.S. Pharmacopia and satisfying the requirements as defined herein can be used for each of the ingredients. Such ingredients, of course, are of well defined scope in view of the high standards under which potential compounds are judged pharmaceutically suitable.

Any drug of appropriate solubility can be formulated in accordance with this invention. Expecially suitable are those for which there exists a specific reason for achieving zero order release and/or other release curve shape effects, such as minimizing peak serum levels. For example, such drugs include antibiotics, cardiovascular agents, analgesics, antipyretics, antiinfectives, antacids, gastrointestinal medications, steroids, CNS stimulants, psychopharmacologic drugs, antineoplastic and immunosuppressive drugs, antihistaminics, vitamins, essential minerals, sympathomimetic and parasympathomimetic drugs, antitussives, diuretics, sedatives, hypnotics, antiepileptics, decongestants, antiasthmatics, etc. (lithium formulations are the subject of the claims of U.S. Pat. No. 4,264,573 mentioned above, and are excluded from the claims of this application.)

By formulating such drugs in accordance with this invention, deleterious high or very slow rates, e.g., sustained release rates, of absorption and/or peak blood levels, or other absorption phenomena associated with toxic and/or adverse side effects, can be avoided. Simultaneously, because the absorption rate can be reduced to precisely desired levels by attainment of a zero order release rate, the serum peak concentration is blunted via the controlled surface erosion of this invention. It is, possible therefor, to increase the unit dosage of the drug and to correspondingly reduce its frequency of administration.

For example, FIG. 1 shows the conventional absorption curve for lithium attained by oral administration of tablets. There is a very large initial absorption peak. However, using the formulations of this invention, a zero order release of lithium is achieved, which is so thoroughly controllable that it can be slowed down sufficiently to lower the initial peak to highly managable levels. The zero order release from the tablet occurs from the zero time point to the peak of the absorption curve. It is during this time that the amount of lithium getting into the blood stream more than compensates for the amount which is being eliminated. At the time corresponding to the peak of the curve, the absorption rate and elimination rate are in dynamic equilibrium. Thereafter, the tablet having released essentially all or most of the active ingredient, the elimination rate is greater than the absorption rate and the blood level decreases. The next dose is administered as soon as this level begins to approach the lower limit of the therapeutic range. By similar control of the release rate for any other drug, similar bluntings of absorption curve peaks and other related effects can be achieved in accordance with this invention.

In general, the amount of the active ingredient will be 10-90% by weight of the tablet, e.g., 30-90%, typically 50-90%. The drug should have a solubility in water (20° C.) of about 1 weight part in 5 weight parts to 1 weight part in 500 weight parts, e.g., 1/10-1/500 w/w. Typically, the solubility is 1/50-1/300 w/w. In general, the half-life of the drug will not be a factor since the formulation of this invention does not produce sustained release but rather slow, controlled release.

In addition to its role as a medicament, the active ingredient also affects the precise release rate which is obtained, primarily by contributing towards penetration control and cohesion because of its solubility.

Ingredient (b) is termed the "surface controller" and functions primarily as a surface uniformity control agent during dissolution and erosion. The selection of a particular agent is not especially critical as long as it is a pharmaceutically acceptable excipient which is of the proper water solubility and compatible with oral tablet manufacturing. Preferably, the agent should have a water solubility (20° C.) of about 1 weight part in 1 weight part to 1 weight part in 40 weight parts; e.g., 1/1-1/20 w/w/. Typically the solubility is $\frac{1}{2}$ to 1/30 w/w. It is usually employed in amounts of 1-40% by weight of the final tablet, typically 3-30 wt %.

Suitable pharmaceutical excipients useful as surface controllers include the generally preferred inorganic compounds such as the chloride, sulfate and phosphate salts of potassium, sodium and magnesium as well as the calcium citrate, phosphate, lactate, gluconate and succinate salts. Suitable organic compounds for use as the surface uniformity control agent include pharmaceutically acceptable mono-saccharides and di-saccharides and the corresponding polyhydroxy alcohols, for example, glucose, fructose, lactose, dextrose, xylose, galactose, sucrose, maltose, sorbitol, mannitol and xylitol. Other candidates include natural amino acids and organic carboxylic or sulfonic acids.

Ingredient (c) is termed the "erosion controller" and serves as the primary erosion rate controlling agent. Consequently, this ingredient generally has a high water solubility, e.g., about 1 weight part in 1 weight part to 1 weight part in 10 weight parts, e.g., 1/1-1/5 w/w, typically 1/1 to 1/5 w/w. Suitable such agents also include pharmaceutically acceptable mono- and di-saccharides and the corresponding polyhydroxy, i.e., polyhydric alcohols, natural amino-acids, and organic carboxylic or sulfonic acids, all of which in general should be suitable for dry mixing with the active granulations or powders. For example, such agents include sorbitol, mannitol, xylitol, lactose, glucose, xylose, galactose, maltose, sucrose, dextrose, fructose, etc. The amount of this ingredient is selected, inter alia, in accordance with the desired rate of dissolution erosion and generally is in the range of 2-20% based on the weight of the final tablet, e.g., 0.1-50, typically 3-10 wt %, e.g., 5-10 wt %.

Ingredient (d) of the inventive composition is termed the "surface activator". Per se, these are fully conventional disintegration agents employed in oral pharmaceutical tablets. However, they are employed in amounts at which they are ineffectual as disintegrating agents. Of course, since the formulations of this invention are to provide slow release, effective amounts of these ingredients would be incompatible. In fact, effective amounts would destroy the controlled erosion phenomenon.

Instead of the conventional disintegrating effect, in the heretofore never used low amounts, these disintegrating agents serve primarily to stabilize the controlled erosion phenomenon over long term storage of the solid compositions. To some degree, they also affect the finally achieved erosion rate, and correspondingly, the release rate. This is probably accomplished through penetration control effects. In other words, without these low amounts of the surface activator, the zero order nature of the release rate of the solid compositions could be accomplished but could not be stably maintained over the long storage periods required in the pharmaceutical field, e.g., 2-5 years, typically 3 years. As can be seen, this is a necessary ingredient in the commercial pharmaceutical tablets of this invention.

Such conventional disintegrating agents include starch and starch derivatives, wood and cotton cellulose derivatives of the microcrystalline or crosslinked types or other polymeric materials etc. which are conventional disintegrants; see, e.g., Shangraw, et. al., Pharmaceutical Technology, October, 1980, pp. 49-57 whose disclosure is incorporated by reference herein. These surface activators are employed in low, disintegrant ineffective but surface activator effective concentrations of 0.05-1.0 wt %, typically 0.05-0.5 wt %.

Ingredient (e) is a surface active agent which is also pharmaceutically acceptable and fully conventional for use in oral tablets. This ingredient provides wettability for any hydrophobic components such as the stearates and also affects medium penetration and surface erosion to some extent. Suitable such conventional surfactants include sodium lauryl sulfate, magnesium lauryl sulfate, dioctyl sodium sulfosuccinate, triethanolamine, polyoxyethylene sorbitan, poloxalkol derivatives and quaternary ammonium salts. In general, the sufactants have hydrophile-lipophile balance ratios (HLB) of above 12. Surface active agents are generally included in the composition in amounts of 0.1-2% by weight of the final tablet, typically 0.15-1.0 wt %.

Under ideal circumstances, ingredients (a)-(e) would be sufficient to achieve all purposes of this invention including zero order release rates for the active ingredient in accordance with the controlled erosion phenomenon. Such five component formulations, however, will be rare since almost all active ingredients require additional excipients to satisfy the demands of the tablet manufacturing steps. Such tableting ingredients include the familiar binders and dye wall lubricants, i.e., ingredients (f) and (g) mentioned above.

Ingredient (f) of the pharmaceutical composition of this invention is a fully conventional pharmaceutically acceptable binder for oral tablets. These are normally employed to aid in the formation of granules during the granulation step(s), to modify the compression characteristics during the compression steps, or to aid during other conventional tablet forming processes. As mentioned, the compositions of this invention achieve slow release at zero order using only the relatively soluble ingredients discussed above. Binders, e.g., gums, waxes, relatively insoluble polymers, etc., previously needed to achieve such slow release rates in conventional sustained release compositions and many other slow release compositions, are obviated. These ingredients are employed only where desirable, or necessary for tableting purposes, per se.

Suitable such fully conventional pharmaceutical binders include povidone (polyvinylpyrrolidone), polyvinylalcohol, polyethyleneglycol, sucrose, lactose, gelatin, starch paste, acacia, tragacanth, etc.

In general, when present, the binders are included in the inventive pharmaceutical composition in amounts of 1-20% by weight, of the final tablet, typically 1-5 wt %. When binders are absent, the composition of this invention will be inherently compressable and/or granulatable, e.g., by the slugging technique or by the addition of a subsequently evaporatable, activating solvent such as water, alcohol, acetone, etc. In addition to the primary binding effect of this ingredient, wettability control and penetration control will sometimes be affected to some degree by its inclusion, depending, of course, on the specific characteristics of the particular binder employed.

Ingredient (g) is a fully conventional, pharmaceutically acceptable die wall lubricant for inclusion in oral tablets. This ingredient is required in order to facilitate the ejection of the tablet from the die after the compression step by lubrication of the tableting tool. Suitable such conventional die wall lubricants include the stearate salts such as calcium, magnesium, and zinc, as well as stearic acid, mineral oil, vegetable oil derivatives, polyethylene glycols, talc, etc. In general, 0.5-5% by weight of the final tablet of this ingredient is included, i.e., amounts in which these ingredients function as die wall lubricants, typically 1-4 wt %.

Ingredients (e) and (g) may also be added to the composition in conventionally combined form. Such combinations are commercially available and are provided as a homogeneous mixture of the two ingredients prepared by spray drying or other techniques. Such commercially available combined lubricants and surface active systems include Stear-o-wet C and Stear-o-wet M.

Very often, an active ingredient is dosed in high concentrations. Typical such high dosage drugs include lithium, theophylline, quinidine sulfate, etc. Such drugs are dispensed in unit dosages from 50-500 mg, for example. For other high dosage drugs, unit dosages are as high as 1000 or 1500 mg. Such dosages are quite readily compatible with the pharmaceutical composition of this invention as defined above. However, it is often desired to formulate drugs in dosage ranges of less than 50 mg, e.g., 1- <50 mg per tablet yet still retain conventionally sized tablets. In such situations, ingredient (h) can be incorporated into the tablet replacing a corresponding amount of the active ingredient per se. In this way, slow release base formulations for the more potent type of drugs can be prepared at low dosages.

Since excipients (h) are used to replace active ingredient (a), they should have the same solubility properties, e.g., water solubilities (20° C.) of about 1 weight part in 5 weight parts to 1 weight part in 500 weight parts, e.g., 1/10-1/500 w/w, typically 1/50-1/300 w/w. The amount of this innocuous bulking excipient, i.e., inert filler, is to be chosen depending upon the desired dosage of the active ingredient as well as on the other factors discussed above with respect to the active ingredient per se. Generally, the amount of ingredient (h) is 1-80% by weight of the finally produced tablet, depending on the desired tablet size.

Such innocuous bulking excipients (fillers) are fully conventional and include the pharmaceutically acceptable excipients for oral tablets such as inorganic salts, both mineral and mineral organic, carbohydrates, proteins, emulsifiable fats and the like. Specific examples include calcium salts, such as the lactate, gluconate, glycerylphosphate, citrate, phosphate monobasic and dibasic, succinate, sulfate and tartrate, as well as the same salts of aluminum and magnesium. Typical such carbohydrates include the conventional mono- and disaccharides as well as the corresponding polyhydric alcohols.

All of the ingredients in all of the categories discussed above, of course, must not only be U.S.P. approved, but must also be fully compatible with the other ingredients, especially the active ingredient and with the treatment of the indication of interest.

The specific proportions of the components of the formulation of this invention for a particular active ingredient will be determined by the release rate characteristics desired, using routine pharmaceutical testing procedures and preliminary experiments where necessary. Every ingredient can have some effect on the finally obtained release rate, depending upon its particular characteristics, e.g., solubility, percentage content, and general physical and chemical properties. As a rule, the erosion controller has the most significant effect upon the finally obtained release rate. An indication of the effect upon release rate and other tablet properties as a result of compositional variations in each ingredient can be ascertained from study of Example 6 below.

As an example of one conventional parametric procedure which can be used to arrive at a formulation corresponding to the desired release characteristics for a given active ingredient, the following general guideline is mentioned. First, the drug for which zero order release is desired is combined with a binder and varying amounts of surface controller in order to prepare several mixtures. The amounts of surface controller can vary over a wide range within the scope of this invention. Each of these mixtures is then made highly homogeneous and converted to a base granulation using conventional procedures. For each of these granulates, several subformulations are prepared each having a different amount of erosion controller which, in general, will be the primary determinant for the release rate. Each of these subformulations can have the same amounts of each of the other ingredients or varying amounts since these ingredients will generally not have a dramatic effect upon the finally obtained rate. In vitro dissolution testing for each of the subformulations will indicate which are likely to yield proper in vivo release rates for the drug. Using the information gathered from this parametric study, if necessary, the formulation can be subsequently fine tuned by repeating the same process over a narrower range of ingredients centered around the best formulation. Once a preferred formulation or several formulations are arrived at, in vivo studies are conducted to assure that the proper dissolution and absorption characteristics have been achieved. Again, if further fine tuning is necessary, this can be accomplished using conventional parametric procedures, e.g., similar to those discussed above. All of these parametric procedures at all stages of the preparation are greatly facilitated by the fact that, as long as each ingredient meets the percentage content requirements defined above, zero order release will be attained. This provides a highly advantageous latitude in selecting a precise zero order rate.

Other parameters which can influence the finally obtained release rate include the particle sizes of the ingredients, especially those which themselves have a major impact upon the release rate, as well as tablet hardness. In general, all ingredients of this invention should be in the fine or very fine ranges as defined in U.S.P. XX, p. 971, i.e., for vegetable and animal drugs, these include nominally designated powders nos. 60–80 and for chemicals nominally designated powders nos. 80–120. It is also greatly preferred that the active ingredient and surface controller be of about the same particle size since, in general, these two ingredients, are initially mixed together with the binder to form a very homogeneous granulate, the homogeneity being optimized by the similarity in particle size. The particle size of the binder is not as important since it goes into solution during this initial homogenization granulation. In general, as the particle sizes become smaller the effect is to decrease the release rate. Parametric procedures such as those outlined above can be used to fine tune the formulation in this regard if necessary. In general, the tablets will be compressed to a hardness of 5–20 kg. The harder the tablet, of course, the slower the release rate. Hardness, thus, can also be used as another mechanism for fine tuning the release characteristics of the formulation using typical parametric procedures.

Since the controlled erosion mechanism of the formulations of this invention is a surface phenomenon, the contour of that surface will also play a role and can also be used to fine tune the precise release rate which is obtained. In other words, the overall shape of the tablet will be a factor. In essence, any shape is suitable for use in conjunction with this invention as long as it permits control of both tablet erosion and surface penetration by the surrounding medium in accordance with the foregoing principles. For example, penny-shaped or pancake-shaped tablets will not be suitable since it is very difficult to control both erosion and penetration for any reasonably long period of time. The ratio of thickness to diameter for such shapes is simply too small for erosion and penetration control. In general, suitable shapes for use in conjunction with this invention can vary anywhere from a sphere to shapes which have ratios of thickness to diameter which are sufficiently larger than those of pancake shaped tablets that the penetration and erosion control of this invention can be achieved. For example, ratios of tablet thickness to tablet diameter of about $0.5 \pm 15\%$ have been found to be highly satisfactory. This range is not meant to be limiting but only to indicate the types of conventional shapes which are appropriate.

As to the absolute size of the tablet, for a given shape, there will be no effect on the relative release, i.e., on the release rate in terms of percentage of active ingredient. However, of course, the larger the size, the larger the absolute amount of ingredient per unit of time that will be released. In other words, tablet size exerts a scalar effect on the release rate curve.

Also influencing the precise zero order release rate achieved will be the manufacturing procedures which are utilized for a given tablet. As noted above, as long as these procedures are maintained consistently from batch to batch, the characteristics of the tablet-tablet and batch-batch release curves will be the same. However, if significant variations in the order or conditions of mixing/blending or in the homogeneity achieved, etc. exist in two different runs, significant variations in release rates can be observed. However, in all cases zero order release will be obtained.

For example, the tables in Example 6 below, show the tablet properties of two formulations having identical percent contents of each ingredient, i.e., the first and ninth rows of the table. In the formulation of column 1 (the control), the die wall lubricant and the surfactant are added in a commercially available preblend. Per this invention, a zero order rate is achieved. In the formulation of the ninth column, the same amounts of these two ingredients are employed, but the surfactant is added to the granulate mix of the binder, the surface controller and the drug. As described in detail below, this granulate is subsequently dried and dry blended with the remaining ingredients, including the die wall lubricant. This significant change in processing effects a significant change in the precise release rate which is obtained, i.e., the rate of the latter formulation is approximately one half that of the control formulation. However, in either case, the rate is zero order and the formulation is otherwise in accordance with this invention. It should also be noted that the tablet-tablet reproducibility for the formulation of the ninth column is not as good as that for the control, illustrating the fact that not all means for fine tuning the rate of a formulation are equivalent. Some affect some characteristics and not others and some affect more than one characteristic. In a given case, simple parametric experiments can be used to determine the best combination of all tablet characteristics which will provide the necessary properties.

The methods used in combining all ingredients into the final tablet will be in accordance with conventional good pharmaceutical manufacturing practices. Using these, another of the major advantages of the formulations of this invention is achieved, i.e., the very good tablet-to-tablet and lot-to-lot reproducibility. The ability to achieve very high batch-to-batch uniformity in among the most advantageous aspects of this invention. This consistency and reliability are especially important for clinical use of the inventive formulations which have been designed for controlled slow release in order to alleviate side effects derived from release rates deviating therefrom. Conventional formulations for such controlled release pharmaceuticals in general do not permit such high precision for inter-unit and inter-batch uniformity. In this regard, as is conventional, the various blending, mixing and tableting steps should be maintained as consistently as possible since the conditions employed can have an impact on the release rate of the finally produced tablet. Consequently, once certain manufacturing details have been determined to be compatible with a given pharmaceutical composition in order to achieve a desired release rate, they should be followed as strictly as possible.

A typical preferred sequence of operations is as follows. Initially, the drug is thoroughly blended with the ingredient selected as the surface controller to form a homogenate. It is then granulated with the appropriate binder/solvent system in order to produce granules using conventional methodology. The amount of solvent (e.g., water) employed during the wet granulation step will, of course, have an impact on the resultant bulk density in the final granulation. Typically, such granulation tapped bulk densities will be within the range of 0.5 g/ml-1.5 g/ml. The dried granules formed are dried, e.g., by tray drying, and then conventionally sized in order to provide an appropriate particle size distribution, e.g., in the fine or very fine range as described above.

The finished granulate is thereafter conventionally dry blended with the erosion controlling agent, the stabilizing surface activator (ineffectual disintegrating agent), the die wall lubricant and the surface active agent in a suitable mixer. The final mixture is compressed into tablets of appropriate and consistent hardness, e.g., 5-20 kg. The compressed tablet may be conventionally coated for esthetic, e.g., taste or marking purposes, if desired. Since the controlled erosion phenomenon of this invention has a surface locus, such coatings will have an effect, albeit very minor. That is, they exert a scalar effect upon the release rate curve, raising or lowering the entire curve when plotted on a released amount/time coordinate system. The shape of the curve is unaffected, as is the precise relative release rate which is achieved. In essence, there is a delay in the onset of the release of the drug by the controlled erosion of this invention.

As is also fully conventional, the in vitro determined dissolution rates and other characteristics are subsequently correlated with in vivo absorption and blood levels. This correlation is also used in quality control in order to ensure batch-to-batch uniformity.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Although lithium formulations are not included in the claims of this application, examples involving lithium formulations manufactured in accordance with the principle of this invention per parent U.S. Pat. No. 4,264,573, are included herein since they illustrate details of the carrying out of this invention which are instructive for its employment with any drug.

EXAMPLE 1

Preparation of lithium carbonate slow release tablets

Desired characteristics:

The conventional lithium formulation is a fast release product. It was desired to reduce the side effects attendant to the administration of such conventional tablets and to reduce the frequency of dosing from the normal 3-4 times a day to 1-2 times a day. Additionally, it was desired to prepare a formulation providing gradual and complete release of lithium ion into the bloodstream, i.e., providing a slow release rate of the active lithium ion. Sustained release mechanisms are not only undesirable since excessively retarded release rates cause diarrhea due to the presence of lithium ion in the lower bowel, but also because the half-life of absorbed lithium is not compatible with sustained release formulation. In addition, it was desired to achieve a release rate which would guarantee complete bioavailability of the lithium ion. It was also highly desirable that the release rate follow zero order kinetics.

Very importantly, it was further desired that the initially high concentration peak of absorbed lithium ion in the blood serum be reduced as significantly as possible, thereby avoiding the adverse side reactions associated therewith and enabling the employment of higher dosages at less frequent intervals.

Additionally, it was preferred that the new lithium dosage form be highly reproducible from batch to batch and be formulatable using only conventional techniques and standard equipment. Lithium, of course, is a well known antidepressant and is often used in the treatment of the manic depressive patient.

New lithium tablet formulated per this invention

It was found that by employing the pharmaceutical composition of this invention, all of these ends could be simultaneously achieved. The tablets are prepared as follows.

Sodium chloride is milled through a Whistler Mill using a small slotted screen. 8,000 grams of this sodium chloride and 60,000 grams of lithium carbonate are charged into a 5 cubic feet Ribbon Blender and blending is carried out for 5 minutes. The blender is discharged and the powder mixture is passed through a Fitzmill at a high speed (hammers). The powder is then returned to the blender and wet granulated (16,000 grams of water) with povidone. The binder solution in water is added while the mixer is running. The resultant wet mass is passed through the Fitzmill (¼ inch, perforated band, hammers forward) at high speed. The resultant mass is trayed and dried overnight (16 hours at 55° C.). The dried mixture is sized through the Fitzmill (2 A with knives at medium speed). The resultant blend is returned to the Ribbon Blender. Sorbitol powder is passed through a 40-mesh screen along with Stearowet C (a combination of calcium stearate and sodium lauryl sulfate). 2,000 grams of the Stearowet C and 8,000 grams of the sorbitol powder are added to the blender along with 200 grams of the sodium starch glycolate and the blend is mixed for 5 minutes. The resultant mixture is compressed into 200,000 tablets using a ⅜" standard concave tooling, uppers plain, lowers plain.

Each tablet weighs 406 mg and has the following composition: lithium carbonate, 300 mg; sodium chloride, 49 mg; polyvinyl pyrrolidone 15 mg; Stearowet C, 10 mg; sorbitol, 40 mg; and sodium starch glycolate, 1 mg. The compressed tablets have a hardness of 8–10 kg, a friability of NMT 0.4% and a thickness of 0.175 inches.

These weight contents correspond to ingredient contents of (a) 73.89, (b) 9.85, (c) 3.70, (d) 9.85, (e) and (f) 2.46, and (g) 0.25. Considering the composition of Stearowet C, the respective contents of (e) and (f) are 2.31% and 0.15%, i.e., 9.4 mg and 0.6 mg. In general, these percentages may vary within the following limits: (a) 70–80%; (b) 5–15%; (c) 2–7%; (d) 5–15%; (e) 0.9–3.3%; (f) 0.1–0.2%; and (g) 0.15–0.35%.

The 200,000 tablets produced can then be optionally coated using conventional procedures. The tablets are placed in Accela-Cota and 10,000 milliliters of a conventional clear film seal solution are sprayed thereon. Subsequently, 30,000 milliliters of a colored film seal (e.g., 1300 grams of Opaspray K-1-1243 in 30,000 milliliters of a clear film seal solution) are sprayed. This is followed by spraying of 10,000 ml of half-strength film and color solution (e.g., 215 grams of the same ingredient in 10,000 ml of half-strength film seal solution). The spraying is finished with 5,000 ml of half-strength film seal solution. The coated tablets are dried in a pan for one hour using 800–1,000 cfm of air at 30°–35° C. They are trayed and dried at 20°–23° C. overnight. After submission of, e.g., 150 tablets to quality control for approval, the tablets are polished in a pan with 2 grams of Carnauba Wax. They are then optionally imprinted and subjected to normal control laboratory procedures for testing, followed by conventional inspection.

EXAMPLE 2

Dissolution properties of lithium formulation

Tablets prepared in several runs using the procedures of Example 1 were tested for their dissolution properties as a function of storage time at 20°–22° C. The results are summarized in the Table below:

| STABILITY STORAGE 20–22° C. | | | | |
|---|---|---|---|---|
| Storage Period | $T_{100\%}$ | K | n | r |
| Run Number 1 | | | | |
| Initial | 106.7 | 2.94 | 9 | 0.9798 |
| 10 mos. | 110.3 | 2.89 | 24 | 0.9956 |
| 21 mos. | 103.2 | 3.03 | 24 | 0.9859 |
| Run Number 2 | | | | |
| Initial | 100.8 | 3.14 | 12 | 0.9864 |
| 3 mos. | 104.5 | 3.01 | 24 | 0.9935 |
| 6 mos. | 98.7 | 3.23 | 24 | 0.9984 |
| 18 mos. | 98.0 | 3.24 | 24 | 0.9960 |
| 24 mos. | 100.7 | 3.19 | 24 | 0.9991 |
| 36 mos. | 95.3 | 3.27 | 24 | 0.9847 |
| Run Number 3 | | | | |
| Initial | 93.6 | 3.45 | 24 | 0.9930 |
| 3 mos. | 94.8 | 3.43 | 24 | 0.9925 |
| 6 mos. | 91.5 | 3.65 | 24 | 0.9992 |
| 12 mos. | 90.7 | 3.66 | 24 | 0.9973 |
| 24 mos. | 90.3 | 3.66 | 24 | 0.9968 |
| Run Number 4 | | | | |
| Initial | 106.0 | 2.95 | 24 | 0.9977 |
| 6 mos. | 105.2 | 2.94 | 24 | 0.9967 |
| 12 mos. | 106.0 | 3.12 | 24 | 0.9975 |
| Run Number 5 | | | | |
| Initial | 97.9 | 3.21 | 24 | 0.9954 |
| 12 mos. | 93.5 | 3.32 | 24 | 0.9975 |
| Statistical Summary | | | | |
| n = 19 | | | 19 | 19 |
| $\Sigma x$ = 1887.7 | | | 61.33 | 18.883 |
| X = 99.35 | | | 3.23 | 0.9938 |
| S = 6.09 | | | 0.25 | 0.0055 |
| RSD = 6.13% | | | 7.74% | 0.55% | where:
$T_{100}$ = Minutes for 100% dissolution
K = Dissolution rate mg/min.
r = Linear correlation coefficient The data demonstrate several of the superior properties of the tablets. The lot-to-lot reproducibility with regard to dissolution rate (K) is excellent, a property which is often difficult to achieve in sustained-or slow-release mechanisms in other types of tablets. The initial values for K for all runs range from 2.94 mg/min. to 3.45 mg/min. The composite statistical data for all measurements show that K has a value of 3.23±0.25 mg/min.

As indicated by the linear correlation coefficient (r), all lots at all stability intervals very closely approximate a perfect zero order dissolution rate. This demonstrates that the controlled surface erosion phenomenon governs the dissolution of the tablet, as desired.

Of course, the data also clearly demonstrate the high storage stability of the tablets for long periods of time up to 3 years.

EXAMPLE 3

Pharmacokinetic Properties of the Lithium Formulations

Tablets prepared in accordance with Example 1 have been subjected to extensive clinical testing. The resultant data is summarized in Am. J. Psychiatry 135:8, 917–922 (1978), whose disclosure is entirely incorporated by reference herein.

Figure 2:
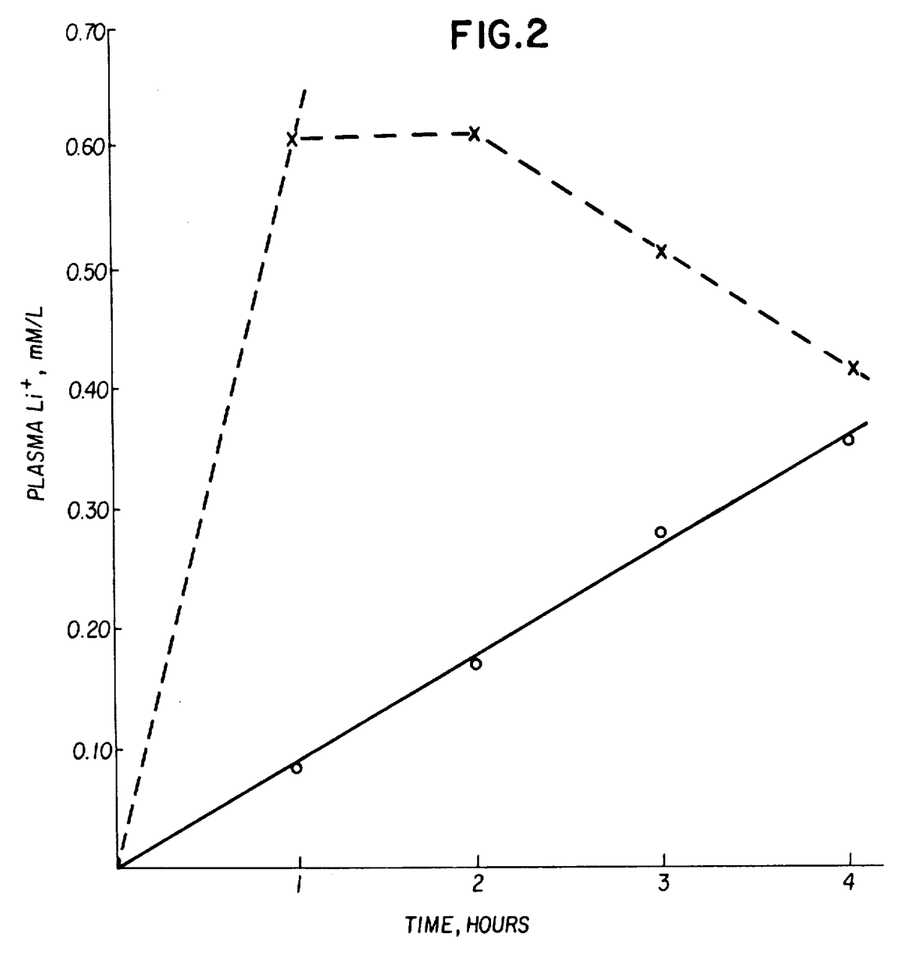
FIG. 2 shows the in vivo absorption rates (single oral dose, mean curve) for the conventional fast release (x-----x) Lithium formulation and the slow release formulation of this invention.

These detailed studies confirmed that the major objectives of the formulation of Example 1 were attained. The in vivo dissolution and absorption of lithium carbonate was controlled as desired in order to reduce serum accumulation rate, reduce maximum serum concentration and permit less frequent dosing. In addition, it was determined that the active ingredient was completely bioavailable without any attendant severe side effects such as diarrhea. Advantageously, the product could be used interchangeably with the conventional fast release formulation except for less frequent administration and more desirable absorption rates. The absorption characteristics of a single oral dosage for both the standard formulation and the slow release formulation of Example 1 may be seen by inspection of FIG. 1. A plot of the first four data points of the FIG. 1 curve for the latter is shown in FIG. 2 (o---------o). The linear plot demonstrates the in vivo zero order uptake of the active ingredient. Comparison of the slope of this line with that of the normal fast release formulation (x-----x in FIG. 2) illustrates the significantly slower release rate, i.e., absorption, rate, achieved.

EXAMPLE 4

Slow Release Formulations for Theophylline

Like lithium carbonate, theophylline is an active ingredient of low to moderate solubility. It is well known as a diuretic, cardiac stimulant, smooth muscle relaxant, and particularly as a bronchodilator to control the symptoms of chronic asthma. Several preparations of this drug having controlled release are commercially available, however, many of these products are reported to give erratic and incomplete absorption; see, e.g., Weinberger et. al., supra. This reference clearly indicates the difficulties which have been encountered in formulating drugs such as theophylline to effect reliable and consistent bioabsorption which is easy to control.

When elimination of theophylline is rapid, excessive fluctuations in serum concentration occur during chronic therapy with conventional fast release dosage forms. This problem is particularly common among children. Typically, conventional dosage units offer little more than an overdose/underdose cycle unless unreasonably short dosing intervals are prescribed. For this reason, many formulators have attempted to slow the rate at which theophylline is released from their products.

Weinberger, et. al. discusses the potential for therapeutic problems related to the bioabsorption of oral theophylline preparations. Four of seven commercially available controlled release theophylline products have questionable bioavailability. All products examined in this publication were found to have first-order absorption rates. First order kinetics are actually incompatible with the concept of controlled release since the rate of absorption is related to the amount of drug remaining to be absorbed. This results in a progressive decrease in absorption as it approaches completion.

However, controlled surface erosion has easily been utilized to alter and control dissolution of theophylline resulting in zero order kinetics. It is possible to produce a series of controlled slow release preparations compatible with the needs of all age groups of patients. Children for example require slower release products than the elderly since absorption and excretion tend to decrease with age.

Middle aged patients would be expected to best utilize a moderately retarded product. Conventional controlled or sustained release mechanisms do not generally allow for a broad range of release characteristics by simple adjustment of ingredient ratios, especially where zero order dissolution exists.

(a) Since side effects such as lower bowel disturbances are absent, the formulation of this drug was set for slower dissolution/erosion than for lithium carbonate in Example 1. Consequently, tablets were prepared following scaled down procedures of Example 1, containing 300 mg/tablet of theophylline and the same proportions of the other ingredients except that the amounts of sodium chloride, povidone and sorbitol powder were reduced to 37.5%, 67% and 50%, respectively, of the amount used in Example 1, and the sodium starch glycolate was omitted to establish that zero order release could be obtained without it.

In vitro data have demonstrated that the controlled surface erosion phenomenon is the mechanism for release of theophylline from these tablets. That is, the statistical data demonstrate that a zero order release rate is involved. However, since the amounts of sodium chloride, povidone and sorbitol are reduced, the rate of dissolution was cut by ⅓. In other words, theophylline dissolved at about 2 mg/min. whereas the product of Example 1 dissolved at about 3 mg/min. Again, dissolution variation among tablets at any sampling interval was very low. The relative standard deviations ranged from ±6.5% at 30 minutes to ±3.1% at 180 minutes when dissolution was essentially completed.

(b) The following formulation of this invention was studied:

| Ingredient | Function | % of Composition |
|---|---|---|
| Theophylline | Drug | 84.39 |
| Sodium Chloride | Surface Uniformity Control | 4.23 |
| Sorbitol | Erosion Rate Control | 5.62 |
| Sod. Starch Glycolate | Surface Activator | 0.14 |
| Sod. Lauryl Sulfate | Surface Active Agent | 0.17 |
| Povidone | Binder | 2.81 |
| Calcium Stearate | Die wall lubricant | 2.64 |

In vitro dissolution data were collected using USP Apparatus I at 100 rpm in 900 ml simulated intestinal fluid without enzymes. The composite dissolution rate for the 6 test tablets was 1.61 mg/min. Statistical analysis of the data by least squares proved that the release rate was zero order since the correlation coefficient was 0.9876. Individual tablets showed very little variation around the mean at any given sampling time. A simple adjustment in formulation (b) by removal of the surface activator, sodium starch glycolate at 0.14%, i.e., formulation (a), showed a significant shift in the dissolution rate curve. This data is compared as follows:

| Comparison of Statistical Release Data | | |
|---|---|---|
| | (a) | (b) |
| Correlation coefficient | 0.9884 | 0.9877 |
| Dissolution Rate | 1.55 mg/min | 1.61 mg/min |
| Half-Life ($T_{50\%}$) | 83 min | 51 min |

Statistical analysis again showed excellent zero order correlation. The rate of dissolution in the absence of the activator was essentially unchanged, i.e., 1.55 mg/min. However, with the activator present, a significantly greater amount of drug is solubilized at the start of the dissolution test. Thus, the half-life of the drug unit was decreased to 60% of that without the activator present.

Figure 3:
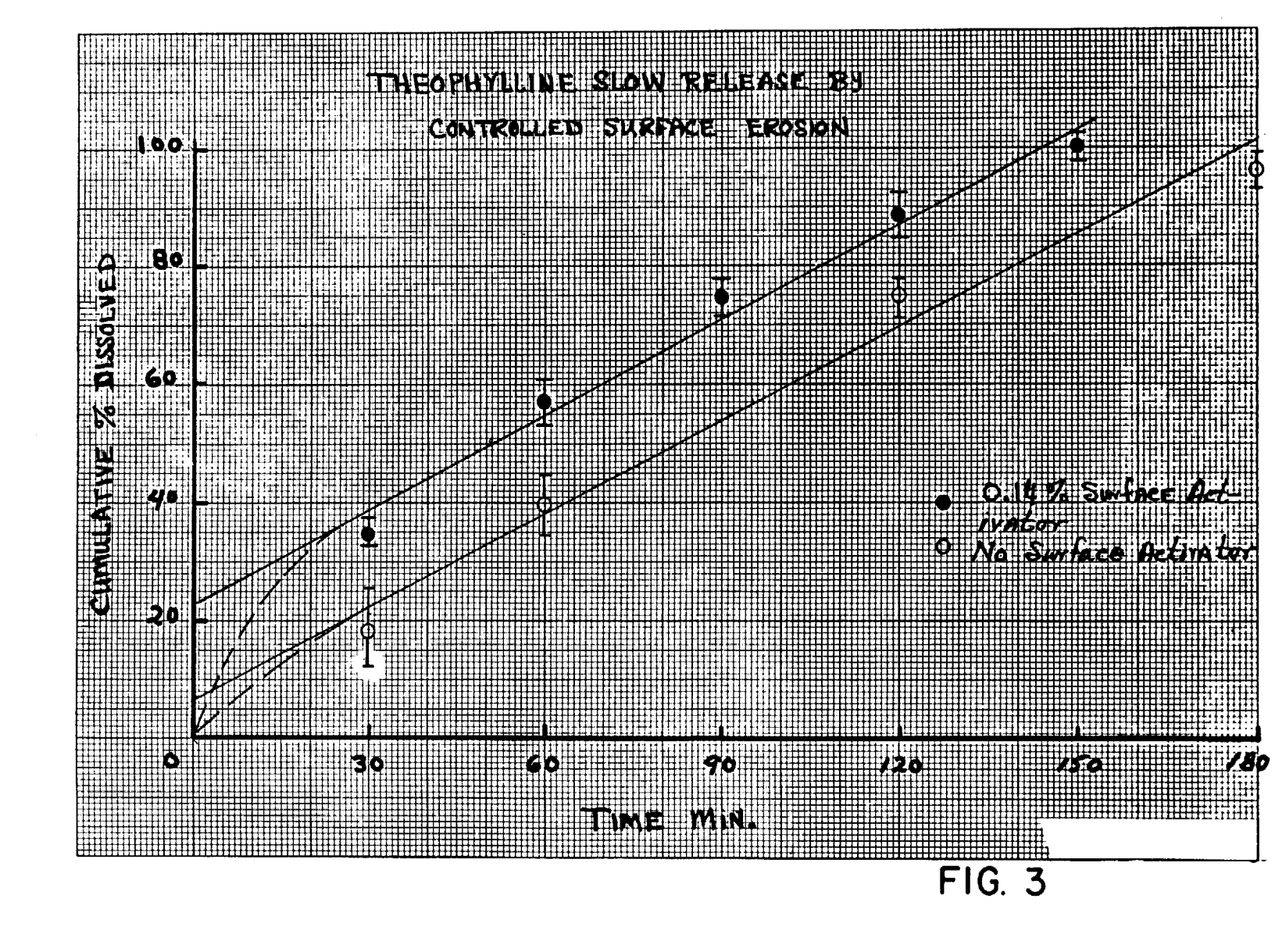
FIG. 3 shows the zero order release rate characteristics of theophylline formulations of Example 4.

This experiment involving a formulation without surface activator, i.e., a formulation excluded from this application in view of commercial requirements concerning shelf life (see above), was performed to demonstrate the effects achieved by varying the amounts of ingredients, i.e., fine tuning the release rate. These data show that it is possible to adjust the dissolution properties of theophylline by minor formula changes. See FIG. 3 (0 formulation (a)—no surface activator; ●formulation (b) 0.14% surface activator). Many other possibilities exist depending upon in vivo results.

EXAMPLE 5

Slow Release Formulations for Quinidine

The solubility of quinidine sulfate in water is reported to be 1 part in 90; thus, this drug, a well known myocardial depressant, is another candidate for the application of the CSE (Controlled Surface Erosion) principle.

The principle and mechanisms described herein were utilized in the development of a slow release quinidine sulfate dosage form. Including the collection of in vitro dissolution data, the entire development required only about 25 man hours using these basic principles.

(a) The previously described compositions were altered with regard to the agent used for controlling surface uniformity and the agent used for the primary control of erosion rate. Substitution of calcium phosphate monobasic and lactose demonstrate the formulation flexibility in the controlled surface erosion principle. Other excipients were the same as those used in examples 1 and 4.

Figure 4:
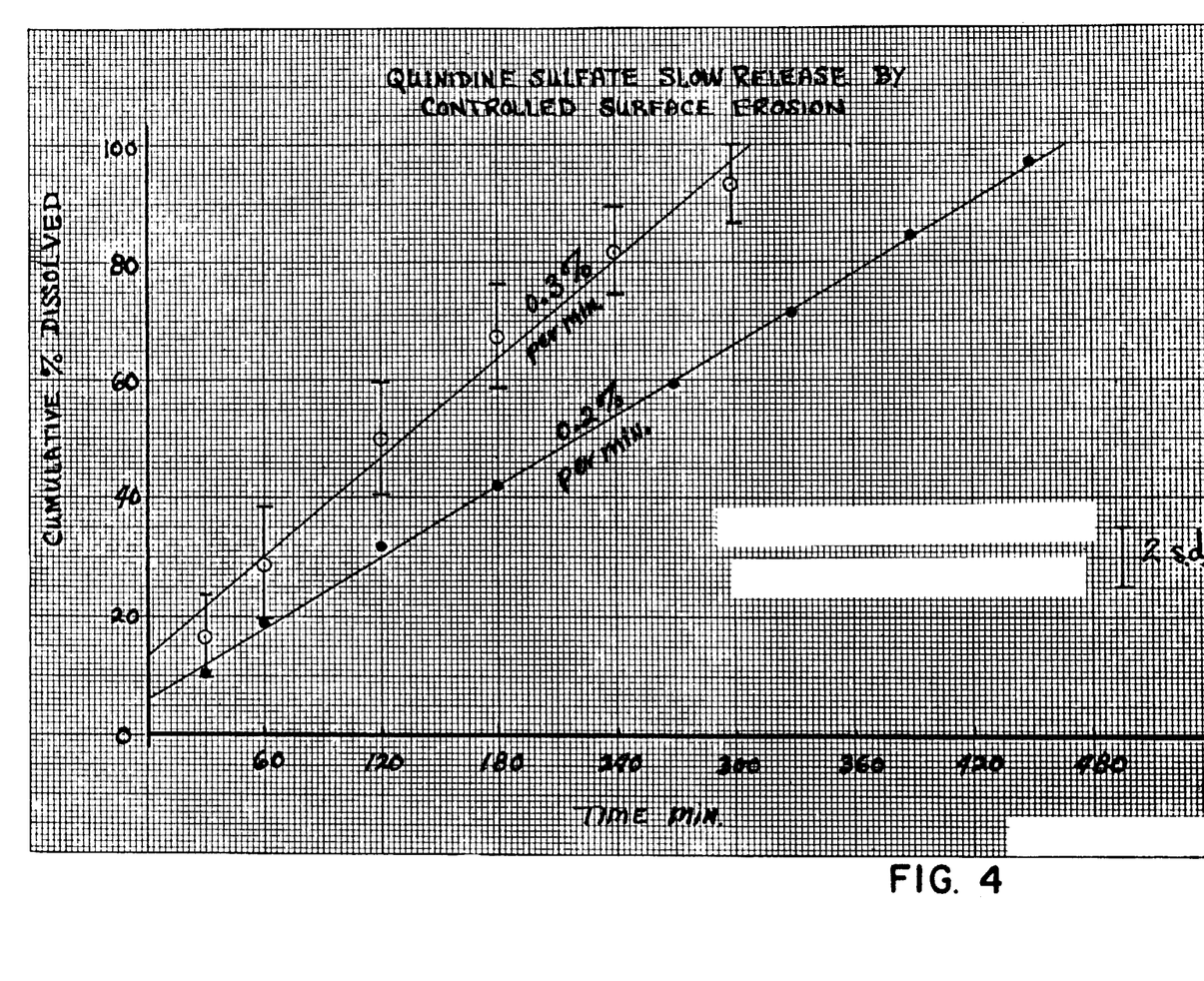
FIG. 4 shows the zero order release rate characteristics of quinidine sulfate formulations of Example 5.

Again, in vitro dissolution analysis showed that release followed a zero order rate since the linear correlation coefficient (r) was 0.9947. The dissolution rate was found to be 0.25%/min. or 0.76 mg/min. from the 300 mg quinidine sulfate tablets. (See FIG. 4; ●formulation (a)). Simple adjustment in the ratios of the calcium phosphate monobasic and the lactose could be made to increase or decrease erosion and dissolution rate depending on in vivo performance.

(b) As a continuation of this study, preparation of alternate formulations has shown the ease with which the in vitro dissolution rate can be controlled by simple adjustment of ingredient ratios. Since the use of sodium chloride with quinidine as the surface uniformity controlling agent would be therapeutically incompatible, monobasic calcium phosphate has been used throughout.

Additionally, these formulations have shown that within the class of ingredients listed as erosion controlling agents, several options are feasible. Thus, it can be seen that lactose and/or mannitol can be easily substituted for sorbitol, the ingredient used above.

The success and acceptability of any dosage form hinges primarily on its consistency and reliability from batch-to-batch and from unit-to-unit. These principles are paramount in dealing with dosage forms designed for controlled, slow, and sustained release. The high degree of release rate consistency for CSE units has again been verified for quinidine sulfate controlled surface erosion units. Conventional techniques used to produce controlled release pharmaceuticals do not usually offer such high precision for inter-unit uniformity.

The following formulation was prepared using the procedures described above.

| Quinidine Sulfate 300 mg Tablets S.R. | | |
|---|---|---|
| Ingredient | Function | % of Composition |
| Quinidine Sulfate | Drug | 70.7 |
| Calcium Phosphate (Monobasic) | Surface Uniformity Controller | 17.7 |
| Mannitol | Erosion Rate Controller | 4.72 |
| Sod. Starch Glycolate | Surface Activator | 0.06 |
| Sodium Lauryl Sulfate | Surface Active Agent | 0.25 |
| Povidone | Binder | 2.65 |
| Calcium Stearate | Die wall lubricant | 3.88 |

In vitro dissolution data were collected using USP Apparatus II at 100 rmp in 900 ml of deaerated water. Statistical analysis by the method of least squares showed that quinidine sulfate dissolved at a zero order rate since the correlation coefficient was 0.9926. The tablets retained their form throughout the in vitro test, becoming continually smaller in size as surface erosion and dissolution progressed.

The small coefficients of variation around the means at each sampling time demonstrated the inter-tablet reliability and uniformity associated with CSE. A graphic presentation of this data shows the averages of 6 tablets, plus or minus two standard deviations. (See FIG. 4; 0 formulation (b)).

Comparison of (a) with (b) demonstrates the flexability of controlled surface erosion to achieve alternate dissolution rate patterns. There is a 30% reduction in the dissolution rate (a) wherein lactose is substituted for mannitol as the rate controller. Though the total concentration of these two agents was nearly identical, differences in rate of solution are apparent. Additionally, other changes in ingredient concentrations contribute in a composite manner to a reduction in dissolution rate for (a) as compared to (b).

| Statistical Release Data for (a) and (b) | | |
|---|---|---|
| | (a) | (b) |
| Correlation Coefficient | 0.9995 | 0.9926 |
| Dissolution Rate | 0.60 mg/min | 0.85 mg/min |
| Half-Life ($T_{50\%}$) | 220 min | 133 min |

In vivo studies can routinely be used to determine that these test formulae produce the desired blood levels. If further adjustments are necessary for increased or decreased dissolution rates, the foregoing principles could readily be utilized to achieve the same.

The following table summarizes controlled surface erosion examples 1, 4 and 5 with regard to composition and concentration flexibility.

| Composition:Concentration (% w/w) | | | | | | | | | |
|---|---|---|---|---|---|---|---|---|---|
| Ingredient Category | Function | EXAMPLE 1 | | EXAMPLE 4 | | | EXAMPLE 5 | | |
| | | Composition | % | Composition | % (a) | % (b) | Composition | % (a) | % (b) |
| (a) | drug | Lithium Carbonate | 73.89 | Theophylline | 84.39 | 84.39 | Quinidine Sulfate | 60.20 | 70.7 |
| (b) | surface uniform- | Sodium Chloride | 9.85 | Sodium Chloride | 4.23 | 4.23 | Calcium Phosphate | 30.10 | 17.7 |

-continued

| Ingredient Category | Function | EXAMPLE 1 Composition | % | EXAMPLE 4 Composition | % (a) | % (b) | EXAMPLE 5 Composition | % (a) | % (b) |
|---|---|---|---|---|---|---|---|---|---|
| | ity controller | | | | | | Monobasic | | |
| (f) | binder | Povidone | 3.70 | Povidone | 2.81 | 2.81 | Povidone | 1.50 | 2.65 |
| (c) | erosion controller | Sorbitol | 9.85 | Sorbitol | 5.62 | 5.62 | Lactose Mannitol | 5.00 | 4.72 |
| (g) | die wall lubricant | Calcium Stearate | 2.31 | Calcium Stearate | 2.64 | 2.64 | Calcium Stearate | 2.58 | 3.88 |
| (e) | surface active wetting agent | Sodium Lauryl Sulfate | 0.15 | Sodium Lauryl Sulfate | 0.17 | 0.17 | Sodium Lauryl Sulfate | 0.17 | 0.25 |
| (d) | surface activator | Sodium Starch Glycolate | 0.25 | Sodium Starch Glycolate | 0 | 0.14 | Sodium Starch Glycolate | 0.40 | 0.06 |

EXAMPLE 6

In order to further indicate how the amounts of ingredients of the formulations of this invention can be readily varied to fine tune the final release rate and yet maintain zero order throughout the ranges recited herein, the following parametric experiments have been performed. See Table.

Despite the radical modifications of single ingredient concentrations, zero order in vitro dissolution was maintained in all cases.

These Examples in toto, demonstrate that the concept of controlled surface erosion can be easily extended to other drugs. The flexibility in selection of excipients to maintain surface uniformity and control erosion rate are clearly established. Most importantly, the achievement

| | Ingredient | | Tablet Amount in mg | | | | | | | | | |
|---|---|---|---|---|---|---|---|---|---|---|---|---|
| (a) | Lithium Carbonate | drug | 300 | 300 | 300 | 300 | 300 | 300 | 300 | 300 | 300 | 300 |
| (b) | sodium Chloride | surface controller | 40 | 20 | 80 | 40[a] | 40 | 40 | 40 | 40 | 40 | 40 |
| (c) | Sorbitol | erosion controller | 40 | 40 | 40 | 40 | 40 | 20 | 80 | 40 | 40 | 40 |
| (d) | Sodium Starch Glycolate | surface activator | 1 | 1 | 1 | 1 | 1 | 1 | 1 | 0 | 1 | 1 |
| (f) | PVP | binder | 15 | 15 | 15 | 15 | 30 | 15 | 15 | 15 | 15 | 15 |
| (g)/(e) | Calcium Stearate/ Sodium Lauryl Sulfate Preblended | dye wall lub/surfactant | 10 | 10 | 10 | 10 | 10 | 10 | 10 | 10 | 0 | 0 |
| (e) | Sodium Lauryl Sulfate | surfactant | 0 | 0 | 0 | 0 | 0 | 0 | 0 | 0 | 0.6[b] | 1.8[b] |
| (g) | Calcium Stearate | dye wall | 0 | 0 | 0 | 0 | 0 | 0 | 0 | 0 | 9.4 | 9.4 |
| | Dissolution Index[c] | | 1.0[d] | 1.08 | 1.16 | 1.09 | 1.75 | 0.89 | 2.63 | 0.63 | 0.53 | 0.97 |
| | Rel. Std. Deviation[e] | | 7.1 | 12.3 | 17.7 | 15.1 | 10.8 | 8.9 | 6.2 | 8.6 | 16.4 | 9.3 |

Figure 5:
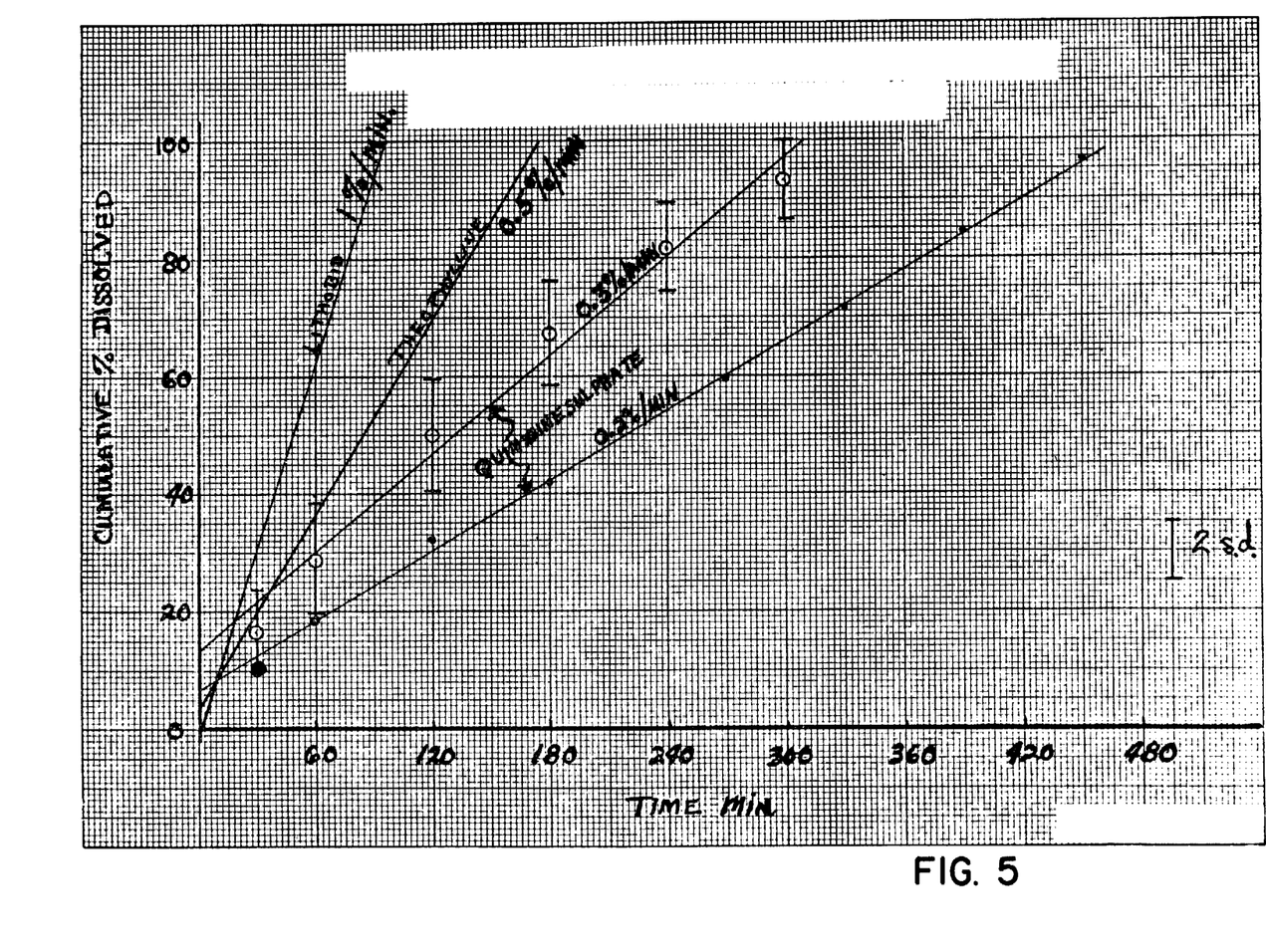
FIG. 5 shows composite release rate curves for formulations of Examples 1, 4 and 5.

[a] 40–80 mesh granules
[b] Dissolve in binder solution
[c] In vitro test at 15 minutes; divide amount dissolved in test formula by amount for control
[d] Control formula
[e] tablet–tablet variation
[f] 94% calcium stearate/6% sodium lauryl sulfate As can be seen, the dissolution rate was substantially increased with the binder (PVP) and the erosion rate controller (sorbitol) were doubled. A significant decrease in dissolution rate occurred when the surface activator, sodium starch glycolate, was removed completely for demonstration purposes or when the surfactant (sodium lauryl sulfate) and the erosion controller were halved. The next most significant effect on dissolution rate occurred when the surface uniformity controller was doubled. Doing so however, threw this particular system out of balance causing a higher amount of tablet-tablet variation. Major adjustments in this element caused only minor average rate changes as compared to the control formula.

and achievability of zero order release for many drugs have been demonstrated. As shown in FIG. 5, which summarizes data from Examples 1, 4 and 5, a very wide range of release rates can be achieved by the formulations of this invention. These extend from the slow release rates which are somewhat slower than conventional fast release rates (left hand side of FIG. 5), to much slower rates effectively limited by the excretion time in the digestive tract (right hand side of FIG. 5.)

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A solid, orally administrable pharmaceutical tablet composition from which the active ingredient has a slow, zero order release rate attained without layers, beads or enteric materials and without relatively insoluble polymers, waxes or gums when administered orally, said tablet being compressed to a hardness of about 5–20 kg, and being either shaped as a sphere, or else having a ratio of tablet thickness to tablet diameter effective to permit tablet erosion and penetration control sufficient for controlled surface erosion thereof, comprising an essentially homogeneous, granulated mixture of:
   (a) an effective amount in the range of about 10–90 wt % of a pharmacologically active compound having a water solubility (20° C.) of about 1/5–1/500 (w/w);
   (b) about 1–40 wt % of a surface controlling compound which is pharmaceutically acceptable in oral compositions and has a water solubility (20° C.) of about 1/1–1/40 (w/w);
   (c) about 2–20 wt % of an erosion controlling compound which is pharmaceutically acceptable in oral compositions and has a water solubility of about 1/1–1/10 (w/w);
   (d) an amount in the range of about 0.05–1.0 wt %, of a surface activator which is a disintegrating agent for pharmaceutical compositions at which amount the compound is ineffective as a disintegrating agent;
   (e) about 0.1–2.0 wt % of a surfactant which is pharmaceutically acceptable in oral compositions and, as necessary for tablet manufacturing purposes;
   (f) about 1–20 wt % of a binder which is pharmaceutically acceptable in oral compositions; or
   (g) about 0.5–5.0 wt % of a die wall lubricant which is pharmaceutically acceptable in oral compositions;
   the pharmacologically active ingredient thus having a slow, zero order release rate when administered orally, and the pharmacologically active compound not being a lithium compound, and not being penny shaped or pancake shaped wherein the ratio of thickness to diameter is too small for erosion and penetration control.

2. A pharmaceutical composition consisting essentially of all of ingredients (a)–(g).

3. A pharmaceutical composition of claim 1 wherein the amounts of ingredients are as follows:
   (a) 50–90 wt %,
   (b) 3–30 wt %,
   (c) 3–10 wt %,
   (d) 0.05–0.5 wt %,
   (e) 0.15–1.0 wt %,
   (f) 1–5 wt %, and
   (g) 1–4 wt %.

4. A pharmaceutical composition of claim 1 wherein ingredient (a) has a water solubility (20° C.) of 1/50–1/300; ingredient (b) has a water solubility (20° C.) of 1/2–1/30; and ingredient (c) has a water solubility (20° C.) of 1/1–1/5.

5. A pharmaceutical composition of claim 1 having a spherical shape or a ratio of tablet thickness to tablet diameter of about 0.5±15%.

6. A pharmaceutical composition of claim 1 wherein all ingredients have a particle size distribution in the fine (U.S.P.) or very fine (U.S.P.) range.

7. A pharmaceutical composition of claim 1 further comprising, in place of a corresponding amount of active ingredient (a), 1–80 wt % of an inert bulking excipient (h), pharmaceutically acceptable in oral compositions and having a water solubility (20° C.) of 1/5–1/500 (w/w).

8. A pharmaceutical composition of claim 1 wherein
   (b) is a chloride, sulfate or phosphate of potassium, sodium or magnesium; calcium citrate, phosphate, lactate, gluconate or succinate; a mono- or di-saccharide or a corresponding polyhydric alcohol; a natural amino acid; or an organic carboxylic or sulfonic acid; and
   (c) is a mono- or di-saccharide or a corresponding polyhydric alcohol; a natural amino acid; or an organic carboxylic or sulfonic acid.

9. A pharmaceutical composition of claim 8 wherein
   (b) is an inorganic salt and
   (c) is a mono- or di-saccharide or a corresponding polyhydric alcohol.

10. A pharmaceutical composition of claim 9 wherein
    (b) is sodium chloride or calcium phosphate monobasic; and
    (c) is mannitol, lactose or sorbitol.

11. A pharmaceutical composition of claim 10 wherein
    (b) is sodium chloride or calcium phosphate monobasic;
    (c) is mannitol, lactose or sorbitol;
    (d) is sodium starch glycolate;
    (e) is sodium lauryl sulfate;
    (f) is polyvinylpyrrolidone; and
    (g) is calcium stearate.

12. A pharmaceutical composition of claim 6 prepared by first wet granulating ingredients (a), (b) and (f) if present, to form a homogeneous granulate; drying the resultant granulate; dry blending the remaining ingredients with the dried granulate and compressing the blend obtained into tablets of a hardness of 5–20 kg.

13. A pharmaceutical composition of claim 1, 3 or 8 wherein active ingredient (a) is theophylline.

14. A pharmaceutical composition of claim 13 wherein (b) is sodium chloride; (c) is sorbitol; (d) is sodium starch glycolate; (e) is sodium lauryl sulfate; (f) is polyvinylpyrrolidone; and (g) is calcium stearate.

15. A pharmaceutical composition of claim 1, 3 or 8 wherein active ingredient (a) is quinidine sulfate.

16. A pharmaceutical composition of claim 15 wherein (b) is calcium phosphate monobasic; (c) is lactose or mannitol; (d) is sodium starch glycolate; (e) is sodium lauryl sulfate; (f) is polyvinylpyrrolidone; and (g) is calcium stearate.

17. A method of orally administering an active ingredient (a) as defined in claim 1 to a patient in need of treatment with (a), such that (a) is released in vivo with a slow, zero order release rate, comprising orally administering to such a patient a pharmaceutical composition of claim 1.

* * * * *